United States Patent [19]
Herzenberg et al.

[11] Patent Number: 5,403,322
[45] Date of Patent: Apr. 4, 1995

[54] DRILL GUIDE AND METHOD FOR AVOIDING INTRAMEDULLARY NAILS IN THE PLACEMENT OF BONE PINS

[75] Inventors: John E. Herzenberg, Owings Mills, Md.; Mark S. Gosney, Memphis, Tenn.; Marietta I. Crosslin, Horn Lake, Miss.; Leonel Dominguez, Germantown, Tenn.

[73] Assignee: Smith & Nephew Richards Inc., Memphis, Tenn.

[21] Appl. No.: 198,465

[22] Filed: Feb. 18, 1994

Related U.S. Application Data

[63] Continuation-in-part of Ser. No. 88,988, Jul. 8, 1993, abandoned.

[51] Int. Cl.⁶ .............................................. A61B 17/56
[52] U.S. Cl. ...................................................... 606/98
[58] Field of Search ................ 606/96, 103, 98, 86, 606/87, 88, 89, 104, 54

[56] References Cited

U.S. PATENT DOCUMENTS
5,152,764  10/1992  Goble ................................... 606/96

FOREIGN PATENT DOCUMENTS
0558789   9/1993  European Pat. Off. .
WO93/11713  6/1993  WIPO .

*Primary Examiner*—Tamara L. Graysay
*Attorney, Agent, or Firm*—Pravel, Hewitt, Kimball & Krieger

[57] ABSTRACT

A drill guide and method for guiding placement of external fixation pins in the bone of a human limb to avoid an implanted intramedullary nail with the drill guide having a plurality of guide holes adapted to guide and receive a bone drill bit and bone pins. The drill guide also includes connecting for connecting the drill guide to one end of a drill guide handle connected to an intramedullary nail implanted in the bone and for aligning the guide holes in a fixed position relative to the nail so that the hole centerlines are oriented to avoid the nail.

15 Claims, 3 Drawing Sheets

DRILL GUIDE AND METHOD FOR AVOIDING INTRAMEDULLARY NAILS IN THE PLACEMENT OF BONE PINS

Cross Reference to Related Applications

This is a continuation-in-part of U.S. Pat. application Ser. No. 08/088,988, filed Jul. 8, 1993, now abandoned, and entitled "Drill Guide And Method For Avoiding Intramedullary Nails In The Placement Of Bone Pins", which is incorporated herein by reference.

BACKGROUND OF THE INVENTION

1. Field of the Invention

The present invention relates to drill guides used in orthopedic surgery, and more particularly to a drill guide apparatus and method for guiding the placement of external fixation pins in the bone of a human limb to avoid an implanted intramedullary nail, wherein a handle attaches to the nail and a drill guide body adjustably connects to the handle so that the position of the drill guide body can be selected to place selected diameter drill sleeve(s) through the body and against the bone tissue.

2. General Background

Limb lengthening and bone transport are often performed with external fixation devices that fix separate bone segments and then displace the bone segments axially. Bone lengthening procedures are performed with a variety of external fixation devices and the success of these procedures is influenced by the mechanical stability of the lengthening system used.

When an intramedullary nail is used in conjunction with the external fixation device the stability of the lengthening system is greatly increased and the success of the lengthening system is enhanced. The external fixation frame is applied after the nail is implanted in the intramedullary canal of the bone being lengthened. The external frame is connected to the bone with various pins and wires and in connecting the frame to the bone it is necessary to place the pins and wires in the bone allowing for adequate bone purchase but without coming in contact with the implanted nail. Presently, the only way to miss the implanted intramedullary nail, when placing the fixation pins and wires in the bone, is by free-handing the insertion of the pins and wires with image intensification.

Drill guides currently available are for guiding bone screws through implanted intramedullary nails for securing the nail in the intramedullary canal of a bone. These drill guide are connected to the implanted intramedullary nail and aid the surgeon in aligning the drill bit with the preformed holes in the intramedullary nail.

With many intramedullary nail drill guides, a handle or some other device is aligned and securely fastened to the exposed proximal end of the implanted intramedullary nail. A second section of the drill guide has guide holes that align with the screw holes in the implanted nail when the guide is placed in proper alignment on the handle. The orientation of the drill guide insures that the holes drilled into the bone will align with the holes in the intramedullary nail for the proper placement of the bone screws.

It would be advantageous to have a radiolucent or radiotransparent drill guide for use in the placement of pins and wires connecting an external fixation frame to a bone that avoids an implanted intramedullary nail. It would also be advantageous to have a drill guide for the placement of bone pins and wires that could be used with any intramedullary nail and external fixation system that allows adequate bone purchase while avoiding the implanted intramedullary nail.

A PCT application (WO 93/11713) relates to a pilot device for a drill for making the drilling for the insertion of a screw in the neck of a femur, an intramedullary nail being already inserted in the femur. The apparatus includes a pivotable drilling template adjustable for height removably fitted at the proximal end of the intramedullary nail and having at least two drilling holes at a horizontal distance from each other of at least the diameter of the intramedullary nail.

SUMMARY OF THE INVENTION

The invention is directed to an improved drill guide apparatus for guiding the placement of external fixation pins in the bone of a human limb while avoiding an implanted intramedullary nail. The drill guide is to be used in conjunction with a proximal drill guide for an intramedullary nail and is generally elongated in shape with a plurality of guide holes adapted to receive a bone drill bit and bone pins. The drill guide has a slotted keyed opening for connecting to the proximal drill guide handle connected to the implanted intramedullary nail. The keyed opening of the drill guide fits into a keyway on the proximal drill guide handle in order to align the guide holes of the drill guide in a fixed position relative to the nail so that the guide hole centerlines are oriented to avoid the implanted nail.

In a preferred embodiment, the guide holes are positioned in two parallel lines on the longitudinal axis of the drill guide and are dimensioned to allow for the placement of a drill sleeve through the guide holes. The guide holes are placed on the drill guide such that the guide can be used on the left or right side of a human body and can be used with any intramedullary nail and external fixation system. Each drill guide hole can be internally threaded to accept a drill sleeve. A serrated guide wire sleeve fits within the drill sleeve. Bracing at the bone site is provided to increase the overall stability of the guide construct due to a "four-bar" frame construct. This is achieved as follows. First, the bone is stabilized with an intramedullary nail. Secondly, the handle is fixed to the intramedullary nail. Third, the drill guide body is locked to the nail handle by tightening a bolt on the guide. Fourth, the drill sleeve is threaded at its proximal end to corresponding internal threads at one of the selected openings of the radiolucent drill guide that accepts the threaded drill sleeve.

The drill sleeve passed through an oversized hole in the guide and threadably attached to the guide. All of the holes on the guide can be internally threaded with threads for engaging the proximal end of the drill sleeve. This creates a locked, stable construct between the guide and the drill sleeve which is unique for drill guides. The drill sleeve is captive to the guide and will not fall out or move relative to the guide.

An inner drill sleeve or guide wire sleeve is slightly longer than the drill sleeve. The inner drill sleeve or guide wire sleeve provides a serrated distal end and a small diameter than the drill sleeve attached to the guide body.

The guide wire sleeve is inserted through the drill sleeve until the serrated tip touches the bone. The wire sleeve guide is struck at its proximal end, causing the serrated end to embed (i.e., bite) the bone creating a rigid fixation point in the overall apparatus and closing the "chain" in the four-bar construct.

The resulting construct attains stability required to prevent the guide wire, drill bit, and pin from walking or skiving off the side of the slippery, rounded contour of the bone, a common problem in the art.

The guide wire sleeve is cannulated to accept a guide wire of a diameter that is 1.8 mm or smaller, for example. A guide wire is first inserted through the guide wire sleeve and purchased into bone to reveal the quality of the site for subsequent drilling to accept the bone pin. The user judges the quality of the wire site using X-ray, and if deemed not acceptable, the small diameter guide wire is removed leaving behind a minor-sized hole in the bone, and a different hole on the guide is then selected.

If a small diameter guide wire (i.e., 1.8 mm or smaller) is not used to judge the quality of the pin site prior to reaming for the pin, than a much larger (for example, 4.8 mm) hole would have to be made and possibly abandoned by the user if deemed inadequate.

Once the small diameter guide wire is deemed acceptable, the guide wire sleeve is pulled out of the drill sleeve and a cannulated drill bit is used in conjunction with the guide wire, remaining in the bone to perform the common familiar procedure of reaming over the guide wire. Once the hole is made, the cannulated drill bit is removed along the guide wire and a bone pin is placed using a locked (i.e., threadably attached) drill sleeve on the guide for guidance to the hole and the bone.

The apparatus of the present invention has multiple, threaded holes positioned longitudinally and laterally on the drill guide body such that it mimics the contour of the femur in the lateral view along the region between the greater trochanter to the lesser trochanter, but not in the mid-diaphysis. These guide holes are aligned with sufficient lateral offset to miss the nail and lie within the available bone in reference to the geometry of the bone at a particular longitudinal level.

This hole positioning incorporated in the guide allows for maximizing the purchase of the bone pin because it targets each hole at the ideal high bone density region between the greater and lesser trochanter as viewed from a lateral direction on the femur.

The radiolucent drill guide body is reversible (i.e., left or right femur). The user simply slides the drill guide body out of the guide handle, turns the drill guide body around and reinserts the guide body through the handle. The same available holes in the guide body can be used to target the other femur.

The present invention also includes a method for guiding the placement of the external fixation pins in the bone of a human while avoiding the implanted intramedullary nail.

BRIEF DESCRIPTION OF THE DRAWINGS

For a further understanding of the nature and objects of the present invention, reference should be had to the following detailed description, taken in conjunction with the accompanying drawings, in which like parts are given like reference numerals, and wherein.

DETAILED DESCRIPTION OF THE PREFERRED EMBODIMENT

Figure 1:
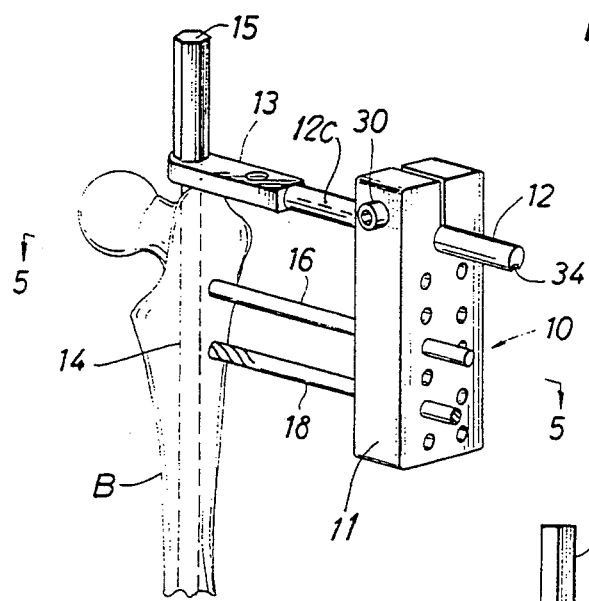
FIG. 1 is a perspective view of the present invention in use on the bone of a human limb.

The present invention is directed to a drill guide to be used in conjunction with a proximal drill guide for an intramedullary nail. In FIG. 1, a patient's femur is designated as bone B, which has an intramedullary canal that receives an intramedullary nail 14 of any diameter, for example from 8mm to 15mm.

Figure 5:
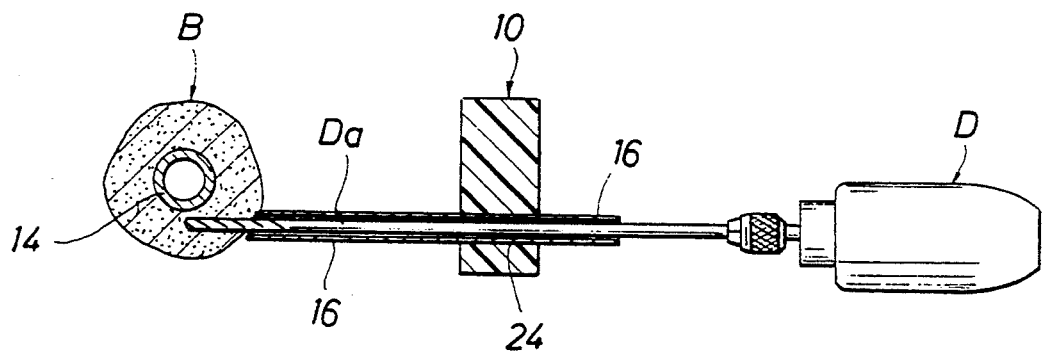
FIG. 5 is a top sectional view of the invention of FIG. 1 illustrating a drill placed through a drill sleeve.

Drill guide apparatus 10 of the present invention is used for guiding the placement of bone pins, self-drilling pins, bone taps and wires used with external fixation devices when an implanted intramedullary nail 14 is part of a limb lengthening system. Drill guide apparatus 10 can place bone pins and wires anywhere on the bone B, but preferably the pins and wires are placed as close as possible to the nail 14, for example within 1 mm of the nail, for maximum bone purchase (FIG. 5). The drill guide 10, with a plurality of preferably cylindrically-shaped guide holes 24, is placed on a proximal drill guide handle 12 that is connected to the implanted intramedullary nail 14 with a bolt 15. Mating key slots between the nail 14 and handle 12 lock together, preventing relative motion (i.e., rotary or otherwise) between these two components of the overall structure. Commercially available intramedullary nails typically do have key slots at the upper or proximal end portion of the nail.

The drill guide body 11 and the handle 12 could also be constructed as a single unit with the handle portion being connected to the implanted intramedullary nail 14 with the bolt 15.

Figure 9:
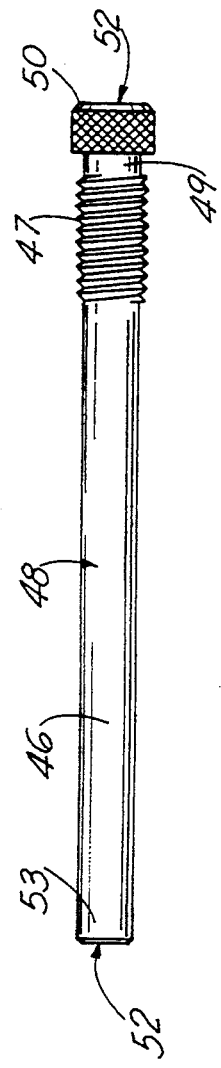
FIG. 9 is a side view of the drill sleeve portion of the preferred embodiment of the apparatus of the present invention.
Figure 10:
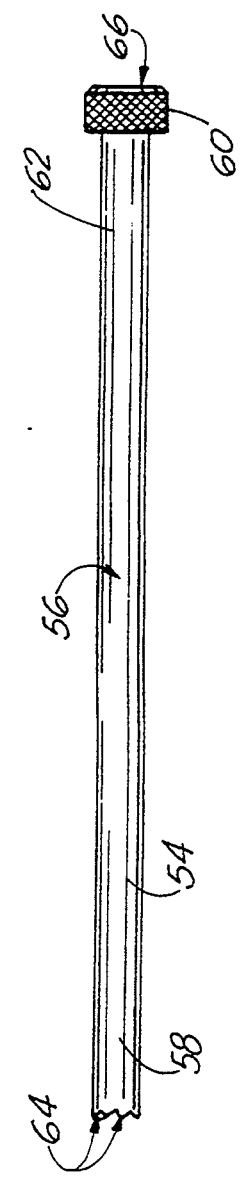
FIG. 10 is a side view of the guide wire sleeve portion of the preferred embodiment of the apparatus of the present invention.

If desired, a drill sleeve 16 can be placed through a selected one of the guide holes 24 for guiding a bone drill D directly to the bone B. The guide holes 24 provide the proper placement of the holes in the bone B of a human limb for receiving the bone pins 18 used in an external fixation system. Threaded drill sleeves can be threadably affixed to the drill guide body (see FIGS. 8–10 as will be discussed more fully hereinafter).

Figure 2:
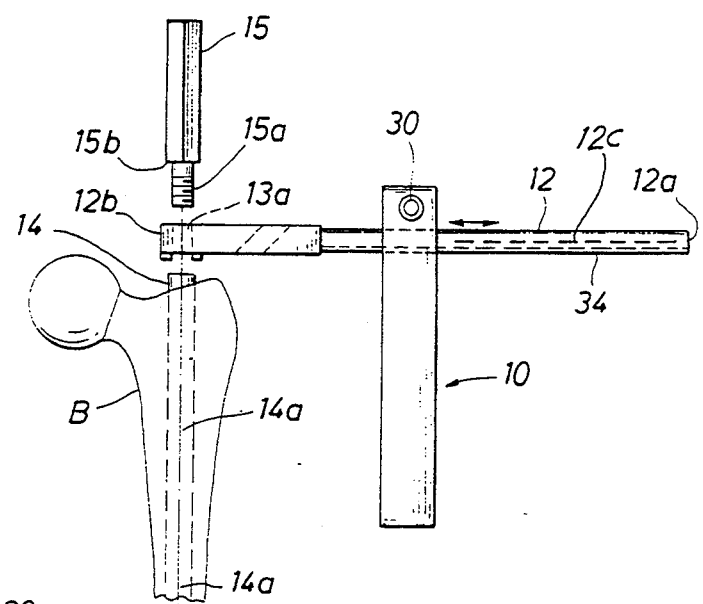
FIG. 2 is an exploded side view of the present invention attached to the handle of a proximal drill guide.

The proximal drill guide handle 12 provides a free end portion 12a and an attachment end portion 12b. The attachment end portion 12b includes enlarged portion 13 having a cylindrically shaped opening 13a. The opening 13a provides an axis that coincides with the central axis 14a of the nail 14 upon assembly which forms a right angle with the central longitudinal axis 12c of the handle 12 (FIGS. 1 and 2).

Bolt 15 provides a lower, externally threaded cylindrical portion 15a that communicates with annular shoulder 15b. The upper proximal end portion of nail 14 provides internal threads that engage the externally threaded portion 15a of bolt 15 during use. The opening 13a is generally cylindrically shaped and slightly larger than the threaded portion 15a of the bolt 15. The externally threaded portion 15a extends through the opening 13a and engages internal threads at the top of the implanted nail 14.

Bolt 15 can provide a hexagonal outer surface as shown in FIG. 1. A surgeon can grip and apply torque to the bolt 15 for firmly affixing the bolt 15 to the top of the nail 14, thereby rigidfying the assembly of bolt 15, drill guide handle 12, and nail 14. In this position, the central longitudinal axis 12c of the drill guide handle 12 forms a right angle with the axis 14a of the nail 14 with the axis 14a being essentially linear at the proximal portion of the nail 14. Drill guide 10 provides a central axis 10a that forms a right angle with the central longitudinal axis 12c of drill guide handle 12 upon assembly. A known geometric relationship between the drill guide 10, drill guide handle 12, and nail 14 is formed upon assembly. FIGS. 1 and 2 illustrate the assembly of the drill guide 10 upon the drill guide handle 12.

Figure 3:
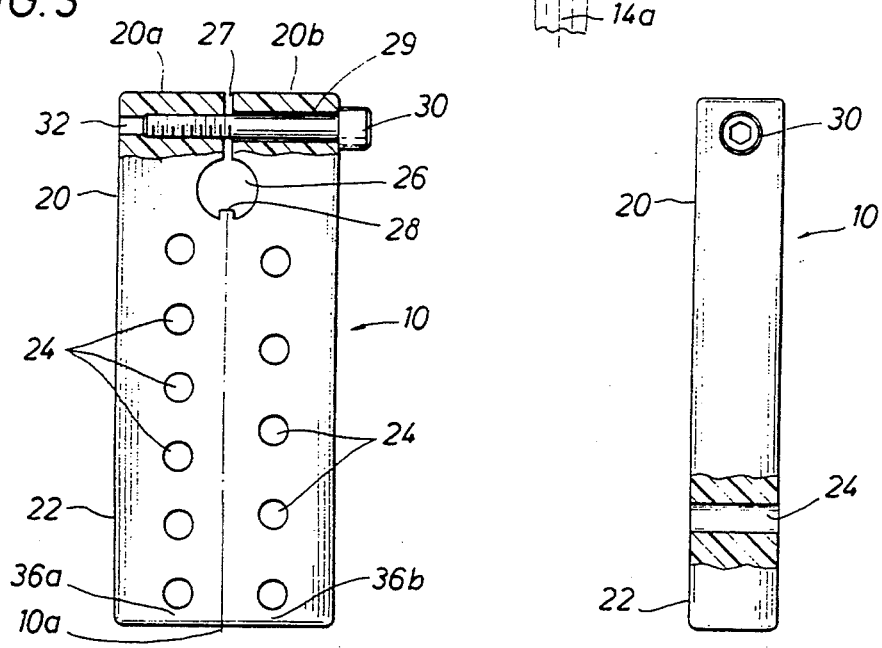
FIG. 3 is a partial cutaway front plan view of the present invention.
Figure 4:
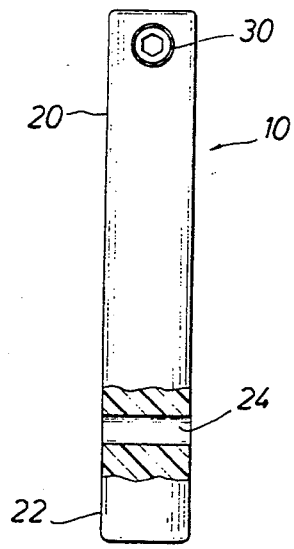
FIG. 4 is a partial cutaway side plan view of the invention of FIG. 3.

In FIGS. 1, 3 and 4, drill guide 10 can be generally in the shape of an elongated block of material, measuring for example approximately 5 inches high, 2 inches across and ¾ inches wide. In a preferred embodiment, the drill guide 10 is formed of a radiolucent or radiotransparent material.

Drill guide apparatus 10 includes drill guide body 11 that has a proximal end 20 and a distal end 22. Proximal end 20 has a pair of opposed portions 20a, 20b separated by opening 26 and slotted portion 27. The proximal end 20 contains a generally cylindrically shaped opening 26 adapted to receive drill guide handle 12. Ridge or key portion 28 is positioned at opening 26 to cooperate with a slot or keyway 34 located on the underside of the handle 12, as illustrated in FIGS. 1 and 2.

An internally threaded opening 32 is positioned on the transverse axis of the portion 20a and a sleeve 29 extends through portion 20b of proximal end 20 of the drill guide body 11. Tightening screw 30 threads through the sleeve 29 and engages the internally threaded opening 32, in order to clamp the handle 12 on the drill guide body 11.

In a preferred embodiment, the plurality of guide holes 24 are oriented on the longitudinal axis of the drill guide body 11 in two parallel rows 36a,b. The two rows 36a,b are positioned on either side of the drill guide body centerline 10a. The guide holes 24 can be positioned on the drill body 11 to accommodate a variety of fixation devices and a kit is provided that contains a plurality of drill guide bodies, for example drill guide bodies 11, 40 for use with a common handle 12. Each drill guide body 11, 40 can have a different guide hole configuration for accommodating a different fixation device.

The keyway 34 on the handle 12 aligns with the centerline 14a of the nail 14. When the opening 26 of the drill guide body 11 is properly placed on the keyway 34, the centerline 14a of the nail 14 is in parallel alignment with the centerline 10a of the drill guide body 11. The guide holes 24 are offset dimensionally from the parallel nail and drill guide centerline axes 14a, 10a such that the guide holes 24 will place the pins 18 on the bone B so as to avoid the implanted intramedullary nail 14 (FIG. 5).

It is necessary for the drill guide body 11 to be positioned on the handle 12 such that the axis of the guide holes 24 are correctly positioned to avoid the nail 14. This correct position may include angling the guide holes 24 or the drill guide 10 to allow for a greater bone purchase of the bone pins 18. The user is thus granted adjustment capability in only one degree of freedom, namely along the handle 12 axis. This feature is important because it allows the user to position the guide body 11 so that the distal end of a drill sleeve that is positioned within any of the multiple guide holes 24 or 42, 43 (FIGS. 8–10) can touch or be near the surface of the bone B to enhance the stability of any guide wire or drill bit used to create an opening in the bone. The site addressed by each hole on the guide will penetrate the surface of the bone B at a variable distance along the handle axis to the curvature of the bone. Therefore, adjustability and the locking feature of the guide body 11 along the axis of the handle 12 achieves a stable platform for the subsequent wire, drill bit, and pin to find its mark on the bone B. Without this feature, hole site placement error is increased because any selected drill sleeve that guides the drill bit or drill wire will in effect be cantilevered at the distal end instead of braced to the bone. The selected drill sleeve thus does not have to physically touch the bone in order to achieve bracing stability. The extra stability is achieved with a secondary guide wire sleeve (see FIGS. 8–10) that enters the drill sleeve as an optional feature.

Additionally, the guide holes 24 are positioned on the drill guide body 11 in such a way as to allow use of the drill guide body 11 on either the left or right side of a human body. The guide holes 24 can be located to accommodate the dimensions of any intramedullary nail and external fixation device as part of a bone lengthening system.

Drill sleeves, which are known in the art, can also be used with the drill guide body 11. As shown in FIG. 1 and 5, a drill sleeve 16 can be placed through the guide hole 24 making contact with the bone B to prevent a drill bit Da of a bone drill D, placed through the drill sleeve 16, from walking or skiving on the bone B.

Figure 6:
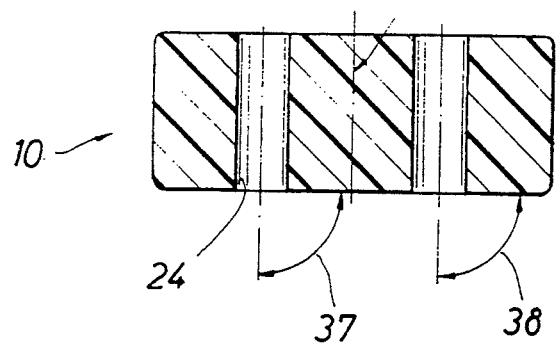
FIG. 6 is a horizontal sectional view of the invention illustrating non-angled guide holes.
Figure 7:
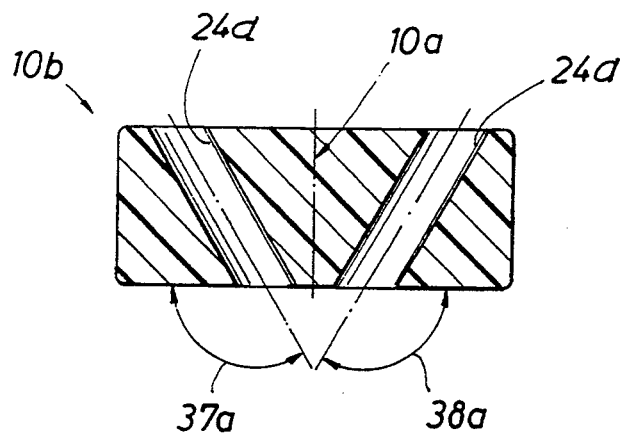
FIG. 7 is a horizontal sectional view of the invention illustrating angled guide holes.

The drill guide 10 can be used at any distance from the bone B if pins 18 are to be placed at right angles 37,38 to the axis of the nail centerline 14a as illustrated in FIG. 6. However, to reduce drill point walking, a drill guide 10b with angled guide holes 24 can be used. As illustrated in FIG. 7, guide holes 24a can be angled towards the nail centerline 14a, at the angle 37a, 38a, in order to approach the surface of bone B more directly with the drill bit Da. The angle 37a, 38a can be in the range of 0° to 50° and angled guide holes 24a require that the drill guide 10b be placed at a fixed distance from the nail 14.

The drill guide is intended to guide pin and wire placement about the proximal or driving portion of an intramedullary nail as the best pin placement anatomically in the femur is generally posterior to the intramedullary canal. However, anterior pin placement is possible, especially at higher angles if using an extension device.

In the placement of the fixation pins, the drill guide body 11 is used in conjunction with a proximal drill guide for an intramedullary nail or the drill guide body 11 and handle 12 can be formed as a single unit. The drill guide body 11 is connected to the proximal drill guide handle 12 that is connected to an implanted intramedullary nail 14. The drill guide body 11 is positioned on the handle 12 such that the keyed opening 26 of the drill guide body 11 engages the keyway 34 on the handle 12. The drill guide body 11 is secured to the handle 12 by tightening the screw 30. A bone drill D is placed through the guide holes 24 and holes are drilled in the bone as close as possible to the nail 14 for maximum bone purchase of the pins 18 without hitting the implanted nail 14 (FIG. 5). The fixation pins 18 are then inserted into the bone B for securing an external fixation device onto the bone B of a human limb.

Figure 8:
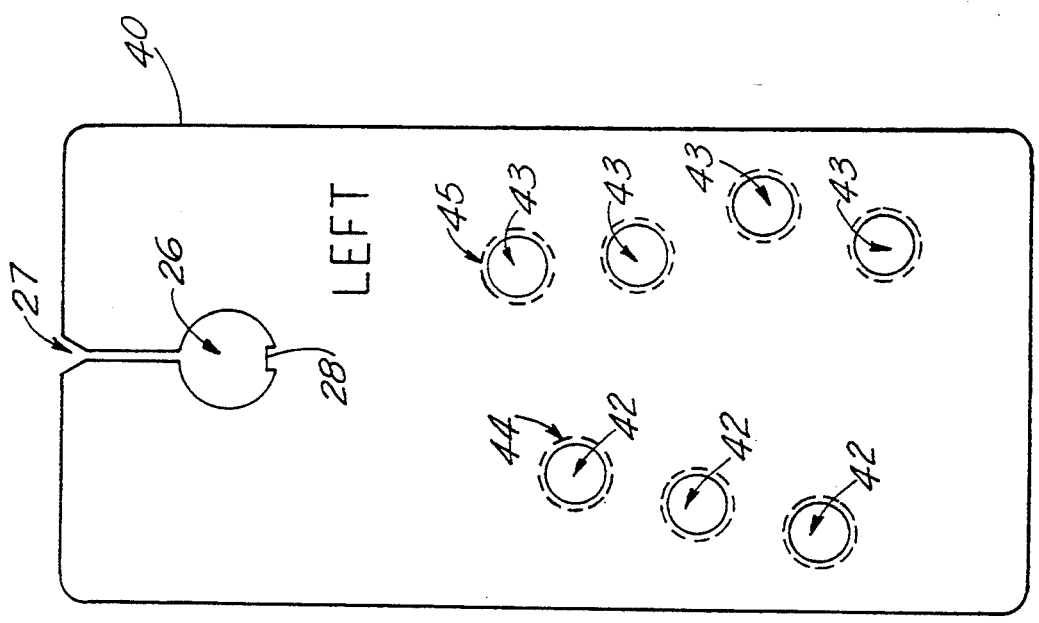
FIG. 8 is a frontal view of the drill guide body illustrating drill guide openings that are internally threaded.

In FIG. 8, the drill guide body 40 is shown having a plurality of guide holes 42, 43 that are internally threaded. The openings 42 provide internal threads 44. The openings 43 provide internal threads 45. The threads 44, 45 correspond to the external threads 47 on drill sleeve 46. Sleeve 46 has a cylindrical outer surface 48.

Drill guide body 40 has opening 26 and keyway 28 for attachment to handle 12.

A gap 27 is provided that communicates with opening 26 as with the drill guide body 11 shown in FIG. 3 so that a bolt 30 can be used to tighten the drill guide body 40 once attached to handle 12 as with the embodiment of FIGS. 1, 3, and 4.

A number of drill sleeves 46 of different sizes can be part of a kit, each sleeve 46 threadably attached during use to a selected threaded opening 42 or 43.

Threads 47 are preferably provided at the proximal end 49 of drill sleeve 46. Drill sleeve 46 provides a longitudinal open ended bore 52 that is cylindrically shaped, corresponding to the external surface 56 of guide wire sleeve 54. The drill sleeve can thus include a second sleeve that occupies bore 52. Drill sleeve 46 has a knob 50 for manipulating the sleeve 46 and for turning the sleeve 46 so that the threads 47 can engage selected threads 44, 45 of openings 42, 43 respectively.

Once the drill sleeve 46 is placed in the desired position, guide wire sleeve 54 can be inserted into bore 52. Bore 52 is a continuous bore that extends between the proximal end 49 of drill sleeve and the distal end 53 thereof. Guide wire sleeve 54 is slightly longer than drill sleeve 46. This allows the distal end 58 of guide wire sleeve 54 to extend beyond the distal end of 53 of drill sleeve 46 during use. Guide wire sleeve 54 provides a knob 60 for manipulating the guide wire sleeve during insertion into the bore 52 of drill sleeve 46. The knob 60 is located at the proximal 62 end of guide wire sleeve 56. The distal 58 end of the assembly of drill sleeve and guide wire sleeve 56 provides a plurality of teeth or serrations 64. Teeth 64 are placed against the bone B and the knob 60 at proximal end 62 is struck with an instrument so that teeth 64 bite into bone B. Guide wire sleeve 54 provides a longitudinally extending open ended cylindrical bore 66 that accommodates a small diameter guide wire (for example, 1.8 mm. or smaller).

Bracing at the bone site to increase the overall stability of the apparatus 10 is achieved due to a "four-bar frame construct". This four-bar frame construct is achieved as follows: first, the bone is stabilized with an intramedullary nail 14 that is inserted in the intramedullary canal of the bone B. Secondly, the handle 12 is fixed rigidly to the intramedullary nail with bolt 15 (see FIGS. 1–2). As a third step, the guide body 11 or 40 is rigidly connected and locked to the nail handle 12 by tightening the bolt 30 on the guide body 11, 40. As a fourth step, a selected drill sleeve 46 is threadably attached at its proximal end 49 to the guide body 40 by engaging the threads 47 of the drill sleeve 46 with selected threads 44 or 45 of the selected guide holes 42 or 43. This attachment of the drill sleeve 46 to the guide body 40 creates a locked, stable construct between the guide body 40 and the drill sleeve 46. The drill sleeve 46 is captive to the guide body 40 and will not fall out or move relative to the guide body 40.

An inner drill sleeve or guide wire sleeve 54 is designed longer than the drill sleeve 46. The guide wire sleeve 54 provides a distal end 58 with teeth or serrations 64. The guide wire sleeve 54 is of a smaller diameter than the drill sleeve so that the external surface 56 of the guide wire sleeve 54 is sized and shaped to fit the bore 52 of the drill sleeve 46.

The surgeon inserts the guide wire sleeve 54 through the drill sleeve 46 until the serrated distal end 58 touches the bone B. A surgeon then strikes the guide wire sleeve proximal end 62 causing the teeth or serrations 64 to be imbedded (i.e., bite) the bone B creating the fourth rigid fixation point of the apparatus 10 enclosing the chain of the four-bar construct. This resulting construct attains stability required to prevent the guide wire, drill bit, or bone pin from walking or skiving off the side of the slippery, rounded contour of bone, known to be a problem without the stability attained with the four-bar construct as above-described.

The guide wire sleeve 56 is cannulated with bore 66 to accept a guide wire of preferably 1.8 mm. diameter or smaller. The guide wire is first inserted through the guide wire sleeve 54 and purchased into bone B to reveal the quality of the site for subsequent drilling to accept the bone pin.

The surgeon judges the quality of the wire site using x-ray, and if deemed not acceptable, the small diameter guide wire is removed. This leaves behind only a minor sized hole in the bone B and a different hole 42 or 43 on the guide 40 can then be selected. If such a small diameter guide wire (i.e., 1.8 mm. or smaller) was not used to judge the quality of the bone pin site, and prior to reaming for the pin, then a much larger (i.e., 4.8 mm.) hole would have to be made and possibly abandoned by the user if deemed inadequate.

Once the small diameter guide wire is deemed acceptable, the guide wire sleeve 54 is pulled out of the drill sleeve 46 and a cannulated drill bit (not shown) is used in conjunction with the guide wire that remains in the bone to perform the common familiar procedure of reaming over a guide wire. Once the hole is made, the cannulated drill bit is removed along with the guide wire and a bone pin is placed using the locked drill sleeve 46 on the guide body 40 for guidance to the hole in the bone.

The guide body 40 preferably has multiple, threaded holes 42, 43 positioned longitudinally and laterally on the guide body 11 such that it mimics the contour of the patient's femur in the lateral view along the region between the greater trochanter to the lesser trochanter, but not in the mid-diaphysis. These guide holes 42, 43 are aligned with sufficient lateral offset to miss the nail 14 and lie within available bone with reference to the geometry of the bone at a particular longitudinal level. The hole positioning incorporated in this guide apparatus 10 allows for maximizing the purchased bone pin because it targets each hole at the ideal high bone density region between the greater and lesser trochanter as viewed from a lateral direction on the femur.

The radiolucent drill guide apparatus 10 of the present invention is reversible (i.e., left or right femur). The users simply slides the selected guide 10, 10b, or 40 from the handle 12, turns it around, and all of the available holes can then be used to target the other femur.

The radiolucent or radiotransparent drill guide of the present invention allows the placement of pins and wires connecting an external fixation frame to a bone while avoiding an implanted intramedullary nail. The drill guide and method of the present invention can be used with any intramedullary nail and external fixation device used in a bone lengthening system.

It should be understood that there can be improvements and modifications made to the embodiments of the invention described in detail above without departing form the spirit or scope of the invention, as set forth in the accompanying claims.

The following table lists the parts numbers and parts descriptions as used herein and in the drawings attached hereto.

| PARTS LIST | |
|---|---|
| Part Number | Description |
| B | bone |
| D | drill |
| Da | drill bit |
| 10 | drill guide apparatus |
| 10a | central axis |
| 10b | drill guide body |
| 11 | drill guide body |
| 12 | drill guide handle |
| 12a | free end portion |
| 12b | attachment end portion |
| 12c | central axis |
| 13 | enlarged portion |
| 13a | cylindrically-shaped opening |
| 14 | intramedullary nail |
| 14a | central axis |
| 15 | bolt |
| 15a | threaded portion |
| 15b | annular shoulder |
| 16 | drill sleeve |
| 18 | bone pins |
| 20 | proximal end |
| 20a | opposed portion |
| 20b | opposed portion |
| 22 | distal end |
| 24 | guide holes |
| 26 | opening |
| 28 | key |
| 29 | sleeve |
| 32 | opening |
| 34 | keyway |
| 36a | row |
| 36b | row |
| 37 | angle |
| 37a | angle |
| 38 | angle |
| 38a | angle |
| 40 | drill guide body |
| 42 | guide hole |
| 43 | guide hole |
| 44 | internal threads |
| 45 | internal threads |
| 46 | drill sleeve |
| 47 | external threads |
| 48 | outer surface |
| 49 | proximal end |
| 50 | knob |
| 52 | bore |
| 53 | distal end |
| 54 | guide wire sleeve |
| 56 | external surface |
| 58 | distal end |
| 60 | knob |
| 62 | proximal end |
| 64 | teeth/serrations |
| 66 | bore |

Because many varying and different embodiments may be made within the scope of the inventive concept herein taught, and because many modifications may be made in the embodiments herein detailed in accordance with the descriptive requirement of the law, it is to be understood that the details herein are to be interpreted as illustrative and not in a limiting sense.

What is claimed as invention is:

1. A drill guide apparatus for guiding placement of external fixation pins in the bone of a human limb while avoiding an implanted intramedullary nail, comprising:
    a) a drill guide body with a plurality of guide holes therethrough, each adapted to receive a drill bit and bone pins;
    b) connecting means for connecting the drill guide body to the intramedullary nail implanted in the bone while aligning the guide holes in a fixed position relative to the nail so that the hole centerlines extend along a side of the nail, enabling a drill to track a selected opening during drilling, and avoid the nail;
    c) the connecting means including a beam having a beam outer surface adapted to extend laterally between the top of the nail and the body; and
    d) the body having a beam opening therethrough that conforms to the outer surface of the beam, so that the body is attachable to the beam at the beam opening, the body being slidably mounted on the beam and movable into multiple lateral positions along the beam, whereby the body may be spaced from the nail axis at a selected distance.

2. The drill guide of claim 1, wherein the drill guide body is elongated in shape with the plurality of guide holes oriented in two parallel rows positioned on the longitudinal axis of the drill guide body.

3. The drill guide of claim 1, wherein the connecting means includes a slotted keyed hole on the body for connecting and aligning the drill guide body on the beam.

4. The drill guide of claim 3, wherein the keyed hole cooperates with a keyway on the beam for aligning the drill guide body with the implanted nail.

5. The drill guide of claim 3, wherein the connecting means includes a screw means for tightening the slotted keyed hole.

6. The drill guide of claim 1, wherein the guide body is formed of a radiolucent or radiotransparent material.

7. The drill guide of claim 1, wherein the plurality of guide holes are positioned on the drill guide body to allow use on a selected side of a human body.

8. The drill guide of claim 2, wherein the plurality of holes are angled in relation to the longitudinal axis of the drill guide body, the angle being in the range of 0° to 50°.

9. A drill guide for guiding placement of external fixation pins in the bone of a human limb while avoiding an implanted intramedullary nail having a central longitudinal axis, comprising:
    a) a drill guide means for guiding a drill bit so that external fixator pin holes can be formed in the bone of a human limb, the drill guide means including a drill guide body with a plurality of guide holes and a handle opening therethrough, each adapted to receive a drill bit and bone pins, the drill guide means having a central longitudinal axis;
    b) connecting means for connecting the drill guide means to the implanted intramedullary nail, while aligning the guide holes in a fixed position relative to the nail so that the hole centerlines extend along a side of the nail, enabling a drill to track a selected opening during drilling, and simultaneously avoid the nail;

c) the connecting means including a drill guide handle having an outer surface adapted to extend laterally between the top of the nail and the drill guide body, a handle free end portion, an attachment portion, and an elongated central portion having a central longitudinal axis;

d) the central longitudinal axis of the drill guide handle forming a first right angle with the central longitudinal axis of the implanted intramedullary nail and the central longitudinal axis of handle forming a second right angle with the central longitudinal axis of the drill guide means when the drill guide means is connected to the free end of the drill guide handle so as to provide parallel alignment of the central axis of the intramedullary nail with the central axis of the drill guide means; and e) the drill guide body handle opening conforming generally to the outer surface of the handle, so that the drill guide body is attachable to the handle at the handle opening;

f) the drill guide body being movable along the length of the elongated central portion of the handle into various adjustment positions, whereby the axis of the nail and body remain in parallel alignment in each adjustment position.

10. A drill guide apparatus for guiding placement of external fixation pins in the bone of a human limb, comprising:

a) an implantable intramedullary nail that can be surgically placed in the intramedullary canal of the patient's bone;

b) a drill guide body with one or more guide holes therethrough, each adapted to receive a drill bit and bone pins;

c) beam means extending between the drill guide body and the intramedullary nail for supporting the drill guide body in a desired position adjacent the patient's limb;

d) connecting means for connecting the drill guide body to the implantable intramedullary nail while aligning the guide holes in a fixed position relative to the nail so that the hole centerlines extend along a side of the nail, enabling a drill to track a selected opening during drilling, and avoid the nail;

e) the connecting means including a beam having an outer surface adapted to extend laterally between the top of the nail and the body;

e) a drill sleeve that interfaces with each of the holes opening; and f) connecting means interlocking the sleeve and the body for preventing longitudinal and lateral movement of the drill sleeve relative to the body.

11. The apparatus of claim 10 wherein the connecting means comprises a threaded connection.

12. The drill guide apparatus of claim 10 wherein the connecting means comprises internal threads on each of the guide holes and a corresponding external thread on the drill sleeve.

13. The drill guide apparatus of claim 10 wherein the drill sleeve is generally cylindrically shaped and provides a distal end portion having teeth thereon.

14. The drill guide apparatus of claim 10 wherein an drill sleeve has an external diameter that is substantially that of the internal diameter of each of the drill guide holes and the connecting means comprises corresponding threaded portions on the drill sleeve and on the drill guide body within each of the guide holes that interlock upon connection of the drill sleeve to the guide holes.

15. The drill guide apparatus of claim 10 wherein the drill guide sleeve has proximal and distal end portions, and the proximal end portion is positioned adjacent the drill guide body upon assembly of the drill sleeve to the drill guide body at the opening.

* * * * *